United States Patent
Ströfer et al.

(10) Patent No.: US 6,433,219 B1
(45) Date of Patent: Aug. 13, 2002

(54) METHOD FOR THE PRODUCTION OF METHYLENEDI(PHENYLAMINE AND METHYLENEDI(PHENYL ISOCYANATE)

(75) Inventors: Eckhard Ströfer, Mannheim (DE); Jan Jacobs, Hoogerheide (NL); Wilfried Seyfert, Kapellen; Hans Volkmar Schwarz, Waterloo, both of (BE); Olaf Schweers, Ludwigshafen (DE); Volker Scharr, Senftenberg (DE); Ulrich Penzel, Tettau (DE)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 09/601,097

(22) PCT Filed: Jan. 26, 1999

(86) PCT No.: PCT/EP99/00472

§ 371 (c)(1),
(2), (4) Date: Sep. 8, 2000

(87) PCT Pub. No.: WO99/40059

PCT Pub. Date: Aug. 12, 1999

(30) Foreign Application Priority Data

Feb. 7, 1998 (DE) .......................................... 198 04 915

(51) Int. Cl.⁷ ............................................. C07C 263/10
(52) U.S. Cl. .................... 560/347; 560/358; 560/359; 564/330; 564/331; 564/333; 564/334
(58) Field of Search ................................. 560/347, 358, 560/359; 564/330, 331, 333, 334

(56) References Cited

U.S. PATENT DOCUMENTS

| 5,053,539 A | 10/1991 | Yano et al. .................. 564/333 |
| 5,286,760 A | 2/1994 | Bolton et al. ................ 521/160 |

FOREIGN PATENT DOCUMENTS

| CA | 2180285 | 12/1996 |
| DE | A 238042 | 8/1986 |
| DE | A 295628 | 11/1991 |
| EP | A-451422 | 10/1991 |
| EP | A-751 118 | 1/1997 |
| GB | 1450632 | 9/1976 |

*Primary Examiner*—Rachel Gorr
(74) *Attorney, Agent, or Firm*—Fernando Borrego; Mary K. Cameron

(57) ABSTRACT

A process for preparing methylenedianiline by reacting aniline with formaldehyde in the presence of acid catalysts comprising, in a semicontinuous process, introducing aniline with or without acid catalyst, feeding formaldehyde with or without acid catalyst through a mixing element into a circuit in which aniline with or without acid catalyst and with or without previously added formaldehyde is circulated and, after feeding in at least 50% of the total amount of formaldehyde to be fed in, heating the reaction mixture to a temperature above 75° C. In addition, the invention relates to a process for preparing polyisocyanates by phosgenation of amines obtainable in this manner and to the polyisocyanates obtainable by this process.

13 Claims, 2 Drawing Sheets

METHOD FOR THE PRODUCTION OF METHYLENEDI(PHENYLAMINE AND METHYLENEDI(PHENYL ISOCYANATE)

The present invention relates to a process for preparing methylenedianiline by reacting aniline with formaldehyde in the presence of acid catalysts, the mixtures which can be prepared by this process comprising methylenedianiline, a process for preparing polyisocyanates by phosgenation of these mixtures comprising methylenedianiline, and polyisocyanates obtainable in this manner.

The preparation of methylenedianiline (also termed MDA below), is generally known and is customarily carried out by continuous or batchwise reaction of aniline with formaldehyde in the presence of acid catalysts. In this reaction, whose main product is 4,4'-MDA, the unwanted byproduct N-methyl-MDA is formed to a small extent. This byproduct is disadvantageous, in particular in the subsequent reaction of the MDA with phosgene to prepare methylenebis(phenyl isocyanate), also termed MDI, since the N-methyl-MDA is the precursor compound for chlorinated byproducts in the MDI and chlorine contents in the MDI as low as possible are sought.

To decrease N-methyl-MDA as byproduct in the preparation of MDA, various processes are known.

Thus, U.S. Pat. No. 5,286,760, for continuous MDA preparation, describes partial neutralization of the reaction mixture between the stage of condensation of two molecules of aniline and one molecule of formaldehyde and the subsequent rearrangement of the intermediate aminobenzylamines, abbreviated as ABA, to give MDA. EP-A 451 442 and DD-A 238 042 disclose, for a continuous process, the addition of formaldehyde over a plurality of process stages. Processes for decreasing the byproduct are also known for batchwise processes. DD-A 295 628 describes the addition of formaldehyde in two steps during the condensation stage, in the first addition the main amount of formaldehyde being added at a low temperature and the second addition of the remaining formaldehyde being performed at the same or higher temperature.

A disadvantage in these processes is the insufficient decrease of the N-methyl-MDA content in the product mixture, so that there is still a need for improvement.

Processes for preparing MDI from MDA by phosgenation are generally known.

It is an object of the present invention to develop a process for preparing methylenedianiline by reacting aniline with formalde-hyde in the presence of acid catalysts which minimizes the N-methyl-MDA content as an unwanted byproduct. Such an MDA should be used, in particular, in an improved process for preparing methylenebis(phenyl isocyanate) (MDI), which should make accessible an MDI having improved properties, in particular a low chlorine content and/or a light color, in particular in the crude MDI which, in addition to the monomeric MDI, also comprises polymeric MDI, and/or should be made accessible in the polymeric MDI.

We have found that this object is achieved according to the invention, in a semicontinuous process, by introducing aniline with or without acid catalyst, feeding formaldehyde with or without acid catalyst through a mixing element into a circuit in which aniline with or without acid catalyst and with or without previously added formaldehyde is circulated and, after feeding in at least 50% of the total amount of formaldehyde to be fed in, heating the reaction mixture to a temperature above 75° C.

This novel procedure permits a higher content of higher MDA oligomers to be obtained than is possible by a continuous procedure at high molar ratios of aniline to formaldehyde without recycling the MDA. By the process according to the invention, minimizing the content of unwanted byproducts is possible.

The reaction according to the invention of aniline with formaldehyde, preferably in the presence of acid catalysts, is performed according to the invention semicontinuously, i.e. one reaction component, the aniline and preferably the acid catalyst, is introduced and the second reaction component, the formaldehyde with or without acid catalyst, is added to the first reaction component. Preferably, the process according to the invention is carried out in such a manner that aniline and acid catalyst are introduced and formaldehyde is added to this first reaction component. The reaction is customarily carried out at temperatures of from 20 to 150° C. Preferably, the process according to the invention is carried out in such a manner that the formaldehyde is added to the reaction mixture in the circuit, i.e. to the aniline, the acid catalyst and to formaldehyde which has possibly been previously added and reaction products, up to an amount of at least 50% of the total amount of formaldehyde to be fed, preferably up to complete addition of all of the formaldehyde, at a reaction mixture temperature in the circuit of from 20 to 75° C., preferably from 20 to 60° C., particularly preferably from 30 to 40° C.

The temperature effects the isomeric distribution of the methylenedianiline in the product. If, preferentially, 2,2'- and/or 2,4'-methylenedianiline are to be prepared, a high temperature may be advantageous. The reaction mixture can be heated by generally customary devices, e.g. by heat exchangers in the pumped circuit or a second pumped circuit and/or via the reactor wall.

The reaction mixture, after feeding into it at least 50% of the total amount of formaldehyde to be fed, is, preferably towards the end of the feed of formaldehyde solution, particularly preferably after the complete addition of the entire amount of formaldehyde to the reaction mixture, heated, preferably for a period of at least 0.2 hours, particularly preferably from 0.2 to 48 hours, in particular from 0.2 to 6 hours, at a temperature of above 75° C., preferably above 90° C., particularly preferably from 105 to 150° C., especially from 110 to 135° C. Particularly preferably, after complete addition of the formaldehyde to the reaction mixture, the reaction mixture can be heated for a period of from 0.1 to 120 minutes at a temperature of from 65 to 100° C. and then, as described above, at a temperature of above 75° C. This heating offers the advantage that the handleability of the reaction mixture is simplified, since the reaction mixture has a lower viscosity at the higher temperature. At the same time, during this heating, unwanted byproducts in the reaction mixture are broken down or rearranged in an ageing phase. The reaction mixture can be aged under these preferred conditions in the apparatus in which the reaction of formaldehyde with aniline was carried out, or else batchwise or continuously in another apparatus into which the reaction mixture can be transferred after complete addition of the formaldehyde. For example, the reaction mixture can be aged in the apparatus in which the formaldehyde solution is fed or was fed. It is also possible to pass the reaction mixture from the apparatus into at least one further reactor, for example a tubular reactor and/or stirred tank, and to perform the ageing in this reactor (these reactors) at a temperature of above 75° C. Preferably, the reaction mixture, after complete addition of the formaldehyde, is transferred to another apparatus in which the ageing is completed. Particularly referably, the reaction mixture, after complete addition of the formaldehyde which took place preferably at a temperature of from 20 to 60° C., particularly preferably from 30 to 40° C., is transferred into a customary storage vessel, heated as described preferably at a temperature of from 65 to 100° C. and then heated in conventional reactors, preferably a tubular reactor, as described preferably at a temperature of from 105 to 150° C., particularly preferably from 110 to 135° C.

The reaction mixture can thus be passed into, for example, tubular reactors, stirred tanks, stirred tank cascades, combinations of stirred tanks and tubular reactors in which the reaction to give MDA can be completed.

The reaction mixture comprising MDA and customarily polymeric MDA can be worked up after the reaction by generally known processes, for example by neutralization, phase separation, distillation and/or chromatographic separation methods, preferably by neutralization, preferably at from 60 to 110° C., and removal of water, aniline and possibly other unwanted minor components by distilling these substances.

Preferably, the reaction mixture is neutralized, preferably with aqueous sodium hydroxide solution, for example 50% strength aqueous sodium hydroxide solution, preferably at from 60 to 110° C., and the aqueous phase is then removed by phase separation. To remove inorganic impurities, the organic phase can be washed at customarily from 60 to 110° C. with water, the aqueous phase can be separated off and then unreacted aniline can be removed from the organic phase, that is to say the MDA, by distillation, preferably at a pressure of from 1050 to 5 mbar and a preferred temperature of from 180 to 240° C.

The starting components formaldehyde, aniline and acid catalyst can be used at customary purities, the formaldehyde being able to be in equilibrium with higher molecular weight addition products such as poly(oxymethylene)glycols. The formaldehyde can be used in customary, for example aqueous, solutions having a formaldehyde content of from 10 to 60% by weight, based on the weight of the solution. The formaldehyde can also be fed in the gaseous state. In this case, it is fed as pure gas or as a mixture with inert gas. If required, water can be added separately.

The reaction mixture can be circulated in a suitable apparatus by generally customary devices, for example pumps. The rate at which the reaction mixture is circulated is preferably from 1 to 6 m/sec. The formaldehyde solution can be fed via a reaction mixing pump, such as described in DE-A 4220239 or via a nozzle system, e.g. a ring-gap nozzle, built into the pump circuit. In the case of the reaction mixing pump, the device not only serves for feeding in the formaldehyde and preferably complete mixing, but also for moving the reaction mixture in the apparatus. If a nozzle is used, the reaction mixture can be moved in the apparatus by conventional pumps known in chemistry. The mixing energy dissipated locally during the feed of formaldehyde into the reaction mixture in the mixing zone of the mixing element, i.e. for example the nozzle or the reaction mixing pump, is preferably from 100 to 100,000 W/l. The quantity in the pumped circuit is in a ratio to the quantity of formaldehyde solution fed into the circuit of preferably at least 20:1.

As acid catalyst, use can be made of catalysts generally known for this reaction, for example acids having a $pKa<1.5$, e.g. mineral acids such as phosphoric acid, sulfuric acid and/or hydrochloric acid (HCl); preferably HCl is used. Aniline and the acid catalyst, preferably HCl, are preferably mixed at from 30 to 60° C, preferably from 35 to 45° C.

The molar ratio of aniline to acid catalyst in the reaction mixture is customarily from 1:0.6 to 1:0.01, preferably from 1:0.3 to 1:0.05. This molar ratio applies in particular to the particularly preferred embodiment in which aniline and acid catalyst are introduced and then formaldehyde and no further acid catalyst is added.

The molar ratio of aniline to the total amount of formaldehyde to be added is customarily from 1.7:1 to 7.2:1, preferably from 1.9:1 to 5.1:1, particularly preferably from 1.9:1 to 3.6:1. The formaldehyde is preferably fed into the circuit through a nozzle or a reaction mixing pump. In order to avoid unwanted parallel reactions leading to byproducts, the formaldehyde is preferably added in such a manner that as rapid and complete mixing as possible takes place with the reaction mixture which is situated in the apparatus. This can be achieved, for example, by generating a turbulent flow in the mixing chamber. In the process according to the invention, preferably in one apparatus, aniline and preferably HCl as acid catalyst are introduced, mixed, circulated, for example by a connected conventional pump, and formaldehyde is added to this reaction mixture, preferably via a reaction mixing pump or nozzle. The formaldehyde can be added in such a manner that constant volumes per unit time are fed into the reaction mixture until there is a suitable molar ratio of aniline to formaldehyde in the reaction mixture. Preferably, the addition is performed in such a manner that, per minute, from 0.05 to 2% of the original volume of the aniline in the apparatus are passed as volume of formaldehyde solution into the reaction mixture. Instead of introducing a constant volume of formaldehyde per unit time, the formaldehyde can be added to the reaction mixture in such a manner that the volume of the formaldehyde added per unit time decreases in accordance with a mathematical function as the addition progresses. Preference is given to an addition rate which is constant, falling linearly, or falling in stages. Furthermore, the formaldehyde can be introduced in pulses into the reaction mixture, in which case a regular or irregular pulse frequency and addition rate can be selected. The total amount of formaldehyde to be introduced should preferably correspond to the molar ratios described at the outset in relation to the amount of aniline. In this batchwise procedure, the reaction mixture is emptied from the apparatus after the desired conversion rate and further worked up if necessary.

DETAILED DESCRIPTION OF THE INVENTION

The reaction according to the invention can be carried out, for example, in an apparatus which has 1: feed lines for aniline and acid catalyst,
2: feed line for formaldehyde,
3: at least one mixing element, for example a reaction mixing pump or nozzle through which the formaldehyde is fed into the apparatus,
4: at least one reactor having
5: optional devices for mixing the reaction mixture,
6: a pipe system which, starting from the reactor, makes circulation of the reaction mixture possible,
7: a device for heating the reaction mixture and
8: an optional pump which circulates the reaction mixture in (6) and
9: at least one connection for taking off the reaction mixture.

Figure 1:
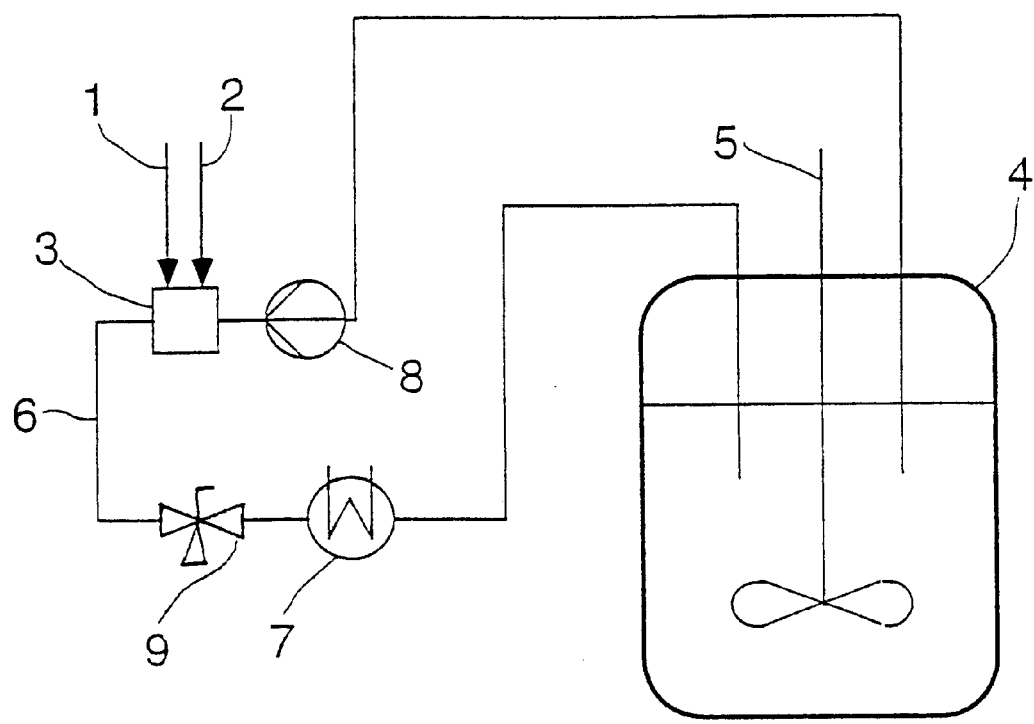
FIG. 1 is a schematic view of an apparatus in which the reaction of the present invention may be carried out.

An apparatus of this type is shown in FIG. 1 by way of example, in which figure it may be noted that aniline and acid catalyst can be added either together, as shown in FIG. 1, or separately, at substantially any point of the apparatus, for example by addition to the reactor (4) or through connections to the reaction mixing pump or nozzle (3). The devices, 7, 8 and, in particular, 9, can also be disposed substantially anywhere, for example, in the case of the connection 9, on the reactor 4 as well.

The selected capacity of the reactor (4) can vary depending on the desired conversion rate. The selected diameter, which can also vary, and the length of the pipe system (6) can also vary substantially as desired depending on batch size. For components (1) to (9) conventional devices can be used, as already described for components (3) and (7). An apparatus suitable for carrying out the process according to the invention can consist of materials customary for this purpose, for example steel/enamel or stainless steel alloys.

The process product, customarily also termed crude MDA, i.e. the mixture comprising methylene- dianiline, for example 2,2'-, 2,4'-, and/or 4,4'-MDA as monomeric MDA, and customarily polymeric MDA, also referred to as polymethylenedianiline, preferably comprises less than 0.09% by weight of N-methyl-MDA and is preferably used for the known synthesis of methylenebis(phenyl isocyanate), known as MDI or diphenylmethanediisocyanate, for example 2,2'-, 2,4'- and/or 4,4'-MDI and polymeric MDI, for example by conventional phosgenation of polyamines.

The phosgenation can preferably be carried out in one or more steps in customary, particularly preferably inert, solvents, e.g. chlorinated aromatic hydrocarbons, for example monochlorobenzene, dichlorobenzenes such as o-dichlorobenzene, p-dichlorobenzene, trichlorobenzenes, the corresponding toluenes and xylenes, chloroethylbenzene, monochlorodiphenyl, alpha- or beta-naphthylchloride and dialkyl phthalates, such as diethyl isophthalate, preferably toluene, mono- and/or dichlorobenzene, in conventional reactors, for example stirred tanks, stirred tank cascades, columns and/or tubular reactors at known temperatures of, for example, from 50 to 150° C., preferably from 70 to 120° C., particularly preferably from 70 to 100° C. and at a pressure of from 0.5 to 10 bar, particularly from 0.8 to 5 bar, particularly preferably from 0.8 to 1.5 bar.

For example, the phosgenation can be carried out by a two-step reaction in the presence of at least one inert orgnaic solvent, the first phosgenation step being carried out in a static mixer and the second phosgenation step being carried out in a dwell-time apparatus, and in the dwell-time apparatus the mass ratios of phosgene to hydrogen chloride being at the same time 10-30:1 in the liquid phase and 1-10:1 in the gas phase.

Static mixers which can be used for the first phosgenation step are the known and abovementioned apparatuses, in particular nozzles. The temperature in the first phosgenation step is customarily from 50 to 120° C., preferably from 60 to 120° C., particularly preferably from 90 to 120° C.

The mixture of the first phosgenation step is preferably fed to a dwell-time apparatus, according to the invention the mass ratios of phosgene to hydrogen chloride in the dwell-time apparatus of the second phosgenation step being at the same time 10-30:1 in the liquid phase and 1-10:1 in the gas phase.

Dwell-time apparatuses which can be used for the process of the invention are known apparatuses, preferably stirring machines, in particular stirred-tank cascades having from 2 to 6 stirred tanks, or towers, in particular those having <10 theroetical plates.

When stirring machines are used as dwell-time apparatuses, as mentioned above, in particular stirred-tank cascades having at least 2, preferably from 2 to 6, particularly preferably from 2 to 5, stirred tanks are used. In principle, a cascade having more than 6 stirred tanks can also be used, but increasing the number of stirred tanks above 6 only increases the equipment required without any measurable improvement in the end product occurring. The mixture of the first phosgenation step customarily enters the first stirring machine at a temperature of 70–120° C., preferably 85–105° C. The temperatures in the stirring machines are preferably, jointly or differing individually, 75–120° C., particularly preferably 80–110° C. The pressures in the stirring machines are customarily individually differing or jointly 1.0–3.0 atm (gauge), preferably 1.2–2.5 atm (gauge).

Particularly preferably, a tower is used as dwell-time apparatus. In this case it is particularly advantageous to operate the tower in counter-current. The product mixture of the first phosgenation step is preferably fed into the tower in such a manner that monomeric MDI/with or without polymeric MDI/solvent/phosgene mixture leaves the tower via the bottom and a phosgene/hydrogen chloride mixture is taken off from the tower overhead and is fed to the hydrogen chloride/phosgene separation. The inlet temperature of the first phosgenation step mixture into the tower can preferably be 80–120° C., particularly preferably 82–117° C. The bottom temperature of the tower is preferably 80–120° C., particularly preferably 90–110° C. The top pressure of the tower is preferably 1.0–4.7 atm (gauge), particularly preferably 2.0–3.7 atm (gauge). The hydrogen chloride/phosgene ratio in the tower is preferably set and controlled by the phosgene excess in the first phosgenation step, the reaction product inlet temperature into the tower, the tower pressure and the bottom temperature of the tower. The amount of phosgene can be fed completely to the first phosgenation step, or only in part, in this case a further amount being fed into the dwell-time apparatus of the second phosgenation step. The tower used preferably has <10 theoretical plates. The preferred use of a valve-tray tower is advantageous. Other tower internals are also suitable which ensure the necessary dwell time for the carbamyl chloride cleavage and rapid and effective removal of hydrogen chloride, for example bubble-cap tray towers, distillation trays having deepened liquid weirs. The perforated tray tower proposed in DE-A 3 744 001 can meet the object of gentle carbamyl chloride cleavage with rapid and effective removal of hydrogen chloride technically only highly inadequately.

The mixtures (crude MDI) prepared by the process of the invention which comprise diphenylmethane diisocyanates (monomeric MDI) and polyphenylene polymethylene polyisocyanates (polymeric MDI) customarily have a diphenylmethane diisocyanate isomer content of from 30 to 90% by weight, preferably from 30 to 70% by weight, an NCO content of from 29 to 33% by weight, preferably from 30 to 32% by weight, based on the crude MDI weight, and a viscosity, determined as specified by DIN 51550 at 25° C., of preferably a maximum of 2500 mPa.s, preferably from 40 to 2000 mPa.s.

The amount of solvent in the phosgenation is expediently such that the reaction mixture has an isocyanate content of from 2 to 40% by weight, preferably from 5 to 20% by weight, based on the total weight of reaction mixture.

Phosgene can be used as such or diluted with gases which are inert under the reaction conditions such as nitrogen, carbon monoxide etc. The molar ratio of crude MDA to phosgene is expediently such that from 1 to 10 mol, preferably from 1.3 to 4 mol, of phosgene are present in the reaction mixture per mol of $NH_2$ groups. In a two-step process, the amount of phosgene can be fed completely to the first phosgenation step or, in part, can also be added to the dwell-time apparatus of the second phosgenation step.

The crude MDI prepared by phosgenation can be purified by customary processes, for example distillation. Preferably, in a first purification operation, phosgene with or without solvent can be removed, preferably substantially, particularly preferably completely, from the phosgenation reaction mixture, i.e. from the crude MDI. This purification step can preferably be carried out by a stripping process. In a stripping process of this type, the crude MDI can be passed into one or more apparatuses having a large internal surface area and can be distributed onto its surface, so that readily volatile components can escape. The apparatus can be, for example and preferably, a falling-film or thin-film evaporator or a packed column of suitable design. Inert gases can be fed in as stripping medium and/or vacuum can be applied over the apparatus. The temperatures during this stripping process are preferably below 210° C., particularly preferably from 50 to 190° C. Preferably, the desired monomeric MDI, for example 2,2'-, 2,4'- and/or 4,4'-MDI and/or mixtures comprising at least two of these isomers, are separated off by a suitable process, preferably by distillation, for example at pressures of from 2 to 50 mbar, preferably from 2 to 20 mbar, and temperatures of from 150 to 250° C., preferably from 180 to 230° C., and/or preferably by crystallization, for example by fractional crystallization.

Particularly preferably, the crude MDI is purified by removing phosgene, HCl with or without solvent, for example in a previously described stripping process, possibly under vacuum or with feed of inert gas, from the crude MDI at a temperature of <150° C., preferably from 50 to 149° C., after preferably complete removal of the phosgene, separating off solvent with or without chlorine-containing compounds from the isocyanate at a temperature of ≦209° C., preferably from 150 to 209° C., particularly preferably ≦109° C., especially from 150 to 190° C, for example in a previously described stripping process, the purification steps being able to be carried out by the previously described apparatuses. Subsequently the desired monomeric MDI, for example 2,2'-, 2,4'- and/or 4,4'-MDI and/or mixtures comprising at least two of these isomers, can be separated off by a suitable process, preferably by distillation, for example at pressures of from 2 to 50 mbar, preferably from 2 to 20 mbar, and temperatures of from 150 to 250° C., preferably from 180 to 230° C., particularly preferably from 210 to 230° C. and/or preferably by crystallization, for example fractional crystallization. The monomeric MDIs are thus preferably separated from the polymeric MDI by distillation and/or crystallization.

The monomeric MDI and/or the polymeric MDI is then conventionally stabilized with an antioxidant based on sterically hindered phenols and/or with at least one aryl phosphite. The stabilizers are expediently used in an amount up to a maximum of 1% by weight, preferably from 0.001 to 0.2% by weight.

Suitable antioxidants based on sterically hindered phenols are, for example: styrenated phenols, that is to say phenols which contain a 1-phenylethyl group in the 2- or 4-position or in 2-and 4- and/or 6-position, bis[2-hydroxy-5-methyl-3-tert-butylphenyl]methane, 2,2-bis[4-hydroxyphenyl] propane, 4,4'-di-hydroxybiphenyl, 3,3'-dialkyl- or 3,3', 5,5'-tetraalkyl-4,4'-di-hydroxybiphenyl, bis[4-hydroxy-2-methyl-5-tert-butylphenyl] sulfide, hydroquinone, 4-methoxy-, 4-tert-butoxy- or 4-benzyl-oxyphenol, mixtures of 4-methoxy-2- or -3-tert-butylphenol, 2,5-dihydroxy-1-tert-butylbenzene, 2,5-dihdyroxy-1,4-ditert-butylbenzene, 4-methoxy-2,6-ditert-butylphenol and, preferably 2,6-ditert-butyl-p-cresol.

Aryl phosphites which have proven useful are tri (alkylphenyl) phosphites having from 1 to 10 carbons in the alkyl radical, for example tri(methylphenyl), tri (ethylphenyl), tri(n-propylphenyl), tri(isopropylphenyl), tri (n-butylphenyl), tri(sec-butylphenyl), tri(tert-butylphenyl), tri(pentylphenyl), tri(hexylphenyl), tri(2-ethylhexylphenyl), tri(octylphenyl), tri(2-ethyloctyl-20 phenyl), tri (decylphenyl) phosphite and preferably tri(nonylphenyl) phosphite, and, in particular, triphenyl phosphite.

These purification processes offer the advantage that chlorine-containing compounds which lead to adverse properties in the desired isocyanate are removed from the isocyanate and at the same time the formation of coloring components is suppressed. In particular, the crude-MDI and, after separating off the monomers, that is to say 2,2'-, 2,4'- and/or 4,4'-MDI, from the crude MDI, the polymeric MDI in the distillation bottoms have according to the invention a light color and a low chlorine content.

The process according to the invention for preparing methylenebis(phenyl isocyanate) can thus be carried out, in a semicontinuous process, by introducing aniline and acid catalyst, the molar ratio of aniline to acid catalyst being from 1:0.6 to 1:0.01, feeding formaldehyde through a nozzle or a reaction mixing pump into a circuit in which aniline and acid catalyst with or without previously added formaldehyde can be circulated at a temperature of from 20 to 75° C., after feeding in at least 50% of the total amount of formaldehyde to be fed in, heating the reaction mixture for a period of at least 0.2 hours at a temperature above 75° C., the molar ratio of the aniline introduced to the total amount of formaldehyde to be added being from 1.7:1 to 7.2:1, neutralizing the resulting methylenedianiline, separating off water and aniline, phosgenating the purified methylenedianiline at a temperature of from 50 to 150° C. and a pressure of from 0.5 to 10 bar in the presence or absence of inert solvents, removing phosgene, HCl and possibly solvent, for example in a previously described stripping process, from the crude MDI at a temperature below 150° C. possibly under vacuum or feeding in inert gas, then separating off solvent with or without chlorine-containing compounds, for example in a previously described stripping process, from the isocyanate at a temperature of ≦190° C. and then separating off the desired monomeric MDI, for example 2,2'-, 2,4'- and/or 4,4'-MDI and/or mixtures comprising at least two of these isomers, by a suitable process, preferably by distillation, for example at pressures of from 2 to 50 mbar, preferably from 2 to 20 mbar, and temperatures of from 150 to 250° C., preferably from 180 to 230° C., and/or preferably by crystallization, for example fractional crystallization.

The MDA and/or the polymeric MDA, for example the crude MDA, can be stored before the phosgenation at a temperature of from 100 to 130° C.

The polyisocyanates prepared using the methylenedianiline according to the invention have the advantage, in particular, that they possess a low hydrolyzable chlorine content. In addition, the isocyanate prepared according to the invention has a color which is desirably very light. These advantages are not only due to the preparation according to the invention of the methylenedianiline having the low byproduct content, but are also due to the fact that the phosgenation of the amines and the product workup are carried out at low pressures and thus low temperatures. This defined combination of many process parameters beginning with aniline to the final bis(isocyanate) leads to the particularly advantageous products according to the invention.

Preferably, the isocyanates and polyisocyanates, for example crude MDI, monomeric MDI and polymeric MDI, particularly crude MDI, especially polymeric MDI, attainable according to the invention, have a hydrolyzable chlorine content of <0.1%, particularly preferably <0.045%, and an iodine color index of <30, particularly preferably <11, at a dilution of 1:5 in monochlorobenzene.

The examples illustrate the invention.

COMPARATIVE EXAMPLE 1

The reaction was carried out in an apparatus which consisted of a stirred-tank cascade having three reactors which had capacities of 700, 800 and 800 ml, and a packed tube. The reaction temperatures in the reactors were set at 40 (first stirred tank), 70 (second stirred tank), 80 (third stirred tank) and 120° C. (tubular reactor) by external cooling and/or heating. The packed tube had a total volume of 5000 ml and an internal tube diameter of 30 mm. The agitator speed in the reactors of the stirred-tank cascade was in each case 500 rpm. 1264 g/h of aniline, which had previously been mixed with 422 g/h of 30% strength aqueous hydrochloric acid, were added to the first reactor. At the first reactor was situated an external pumped circuit having a static or dynamic mixer into which 341 g/h of a 50% strength formaldehyde solution in water were added by a pump. The product mixture from the tubular reactor was neutralized using sodium hydroxide solution. Phase separation was then performed at a temperature of from 70 to 80° C. The organic phase was separated off and washed with 1.5 times the volume of warm water. Excess aniline was distilled off from this purified phase under reduced pressure and recirculated to the first reactor. 24 h after starting up the plant, the reaction mixture was in a steady state and samples of the organic phase were taken. The N-methyl-MDA content in the resulting product was 0.26% by weight. This polyamine was reacted in two stages with phosgene in a conventional process for preparing isocyanates. The hydrolyzable chlorine content in this polyisocyanate was 0.22%.

EXAMPLE 1

Figure 2:
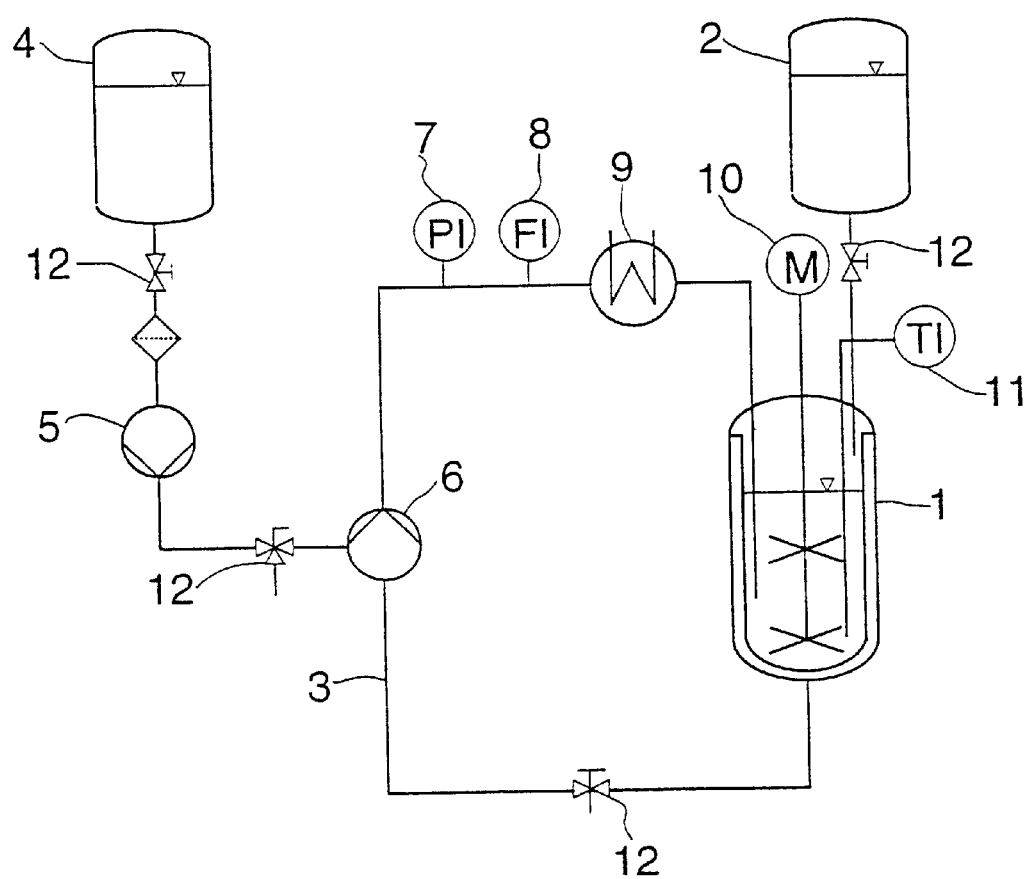
FIG. 2 is a schematic view of another apparatus in which the reaction of the present invention may be carried out.

An apparatus as shown in FIG. 2 was employed. In this FIG. 2, the reference numbers designate the following:

| |
|---|
| 1: reactor |
| 2: reservoir tank, feed of aniline and HCl |
| 3: reaction mixture circulation circuit |
| 4: reservoir tank, feed of formaldehyde solution |
| 5: metering pump |
| 6: mixing element, formaldehyde solution admission |
| 7: pressure gage |
| 8: flowmeter |
| 9: heat exchanger |
| 10: agitator |
| 11: temperature measurement |
| 12: stopcock |

The reactor 1 had a capacity of 1000 ml. The agitator speed was 500 rpm. The external circulation 3, reaction mixture circulation rate approximately 130 l/h, was operated by a pump. 735 g of aniline were introduced from the reservoir tank and mixed with 243 g of 30% strength aqueous hydrochloric acid in reactor 1. At a temperature of 40° C., a total of 204 g of a 50% strength solution of formaldehyde in water was then added within one hour at a constant metering rate to the circuit via the mixing element 6, a dynamic mixer. Directly after the addition of the formaldehyde solution, the reaction mixture was heated and then kept at 120° C. for 2.5 hours. The reaction mixture was worked up as described in comparative example 1. The N-methyl-MDA content in the resulting product was 0.07% by weight. This polyamine was reacted with phosgene in a two-stage process in the process according to the invention for preparing isocyanates. The hydrolyzable chlorine content in this polyisocyanate was 0.06%.

EXAMPLE 2

The procedure of Example 1 was followed, but the formaldehyde solution was added in a staged manner. In the first 30 minutes of the addition, the formaldehyde solution was metered into the reaction mixture at a rate of 306 g/h, and in the second 30 minutes at a rate of 102 g/h. The reaction mixture was worked up as described in Example 1. The N-methyl-MDA content in the resulting product was 0.08% by weight. This polyamine was reacted with phosgene in a two-stage process in a process for preparing isocyanates at a temperature of 80° C. and a pressure of 1 bar. The hydrolyzable chlorine content in this polyisocyanate was 0.07%. The iodine color index of the isocyanate was 15 at a dilution of 1:5 with monochlorobenzene.

The object of developing a process by which the undesired formation of N-methyl-MDA is prevented, could thus be achieved by the process according to the invention. Not only was the content of undesired N-methyl-MDA markedly decreased by 73 or 69%, but also the hydrolyzable chlorine content in the polyisocyanate which was produced using the MDA prepared according to the invention was drastically reduced by >70%. The object of preparing an isocyanate as light as possible starting from MDA was also achieved.

Both the MDA prepared according to the invention and the polyisocyanate produced using this MDA thus displayed substantially improved properties.

EXAMPLE 3

MDA was prepared in an apparatus as shown in FIG. 2 and as described in Example 1. The reactor had a volume of 45 m$^3$. The storage vessel 2 was charged with a mixture of 17,130 kg of aniline and 5378 kg of 30% strength aqueous hydrochloric acid which was then transferred to reactor 1. The agitator speed was 70 rpm. The reaction mixture was agitated in the circuit 3. The circulation rate of the reaction mixture in the circuit 3 was 300 m$^3$/h. At a reaction mixture temperature of 40° C., in the course of 60 min at a constant metering rate, in total 6620 kg of a 50% strength solution of formaldehyde in water were added to the circuit via a mixing nozzle as mixing element 6. The reaction mixture was heated via a heat exchanger 9. After complete addition of the formaldehyde, the reaction mixture was heated to 90° C. and then charged into a storage vessel having a volume of 70 m$^3$. From this storage vessel, the reaction mixture was transferred via a heating device, with which a reaction mixture temperature of 130° C. was set, into a tubular reactor. The dwell time in the tubular reactor was 150 min. The mixture was then neutralized at 103° C. with 50% strength aqueous sodium hydroxide solution and the organic phase was separated from the aqueous phase. To remove inorganic impurities, the organic phase was washed with water at 95° C. and separated from the aqueous phase. Excess aniline was removed from the organic phase in a three-stage distillation at from 180 to 240° C. and a pressure of from 1050 to 5 mbar.

The resultant MDA had an N-methyl MDA content of 0.09% by weight, and the hydrolyzable chlorine content was 0.04 ppm. The MDA was then reacted with phosgene at 80° C. and a pressure of 1.5 bar in a stirred-tank cascade having a dwell time of 60 min. The molar ratio of MDA to phosgene was 1:5.2. The phosgenation was carried out in the presence of 15% by weight of monochlorobenzene, based on the total weight of the reaction mixture. After the phosgenation, HCl and phosgene were removed at 138° C. and a pressure of 1.2 bar, and then solvent and, if appropriate, chlorine compounds, were separated off at 180° C. and a pressure of 70 mbar. The resulting crude MDI was separated by distillation at a pressure of 6 mbar and a temperature of 217° C. into polymeric MDI (PMDI) and monoemric MDI (2,2'-MDI, 2,4'-MDI and 4,4'-MDI). The PMDI produced had a hydrolyzable chlorine content of 400 ppm and an iodine color index of 10 at a dilution of 1:5 in monochlorobenzene.

We claim:

1. A process for preparing methylenedianiline comprising reacting aniline with formaldehyde in the presence of an acid catalyst, further comprising, in a semicontinuous process, introducing said aniline with or without said acid catalyst, feeding formaldehyde with or without acid catalyst through a mixing element into a circuit in which aniline with or without acid catalyst and with or without previously added formaldehyde is circulated and, after feeding in at least 50% of the total amount of formaldehyde to be fed in, heating the reaction mixture to a temperature above 75° C.

2. A process as claimed in claim 1, wherein the formaldehyde is added up to an amount of at least 50% of the total amount of formaldehyde to be added at a temperature of the reaction mixture in the circuit of from 20 to 75° C.

3. A process as claimed in claim 1 or 2, wherein the molar ratio of aniline to acid catalyst is from 1:0.6 to 1:0.01.

4. A process as claimed in claim 1, wherein the molar ratio of aniline to the total amount of formaldehyde to be added is from 1.7:1 to 7.2:1.

5. A process as claimed in claim 1, wherein the formaldehyde is fed into the circuit via a nozzle or a reaction mixing pump.

6. A process as claimed in claim 1, wherein the reaction is carried out in an apparatus which has
1: feed lines for aniline and acid catalyst,
2: feed line for formaldehyde,
3: at least one reaction mixing pump or nozzle through which the formaldehyde is fed into the apparatus,
4: at least one reactor with or without
5: devices for mixing the reaction mixture,
6: a pipe system which, starting from the reactor, makes circulation of the reaction mixture possible,
7: a device for heating the reaction mixture and
8: an optional pump which circulates the reaction mixture in (6) and
9: at least one connection for taking off the reaction mixture.

7. A process for preparing polyisocyanates by phosgenation of methylenedianiline, prepared by reacting aniline with formaldehyde in the presence of acid catalysts, further comprising, in a semicontinuous process, introducing said aniline with or without said acid catalyst, feeding formaldehyde with or without acid catalyst through a mixing element into a circuit in which aniline with or without acid catalyst and with or without previously added formaldehyde is circulated and, after feeding in at least 50% of the total amount of formaldehyde to be fed in, heating the reaction mixture to a temperature above 75° C.

8. A process for preparing methylenebis(phenyl isocyanate), MDI, as claimed in claim 7, which comprises phosgenating methylenedianiline at a temperature of from 50 to 150° C. and a pressure of from 0.5 to 10 bar, in the presence or absence of inert solvents.

9. A process as claimed in claim 8, wherein the crude MDI prepared by phosgenation is purified in such a manner that phosgene and optionally solvent are removed in a first purification step and then the desired monomeric MDI is separated off by distillation and/or by crystallization.

10. A process for preparing methylenebis(phenyl isocyanate), comprising, in a semicontinuous process, introducing aniline and acid catalyst, the molar ratio of aniline to acid catalyst being from 1:0.6 to 1:0.01, feeding formaldehyde through a nozzle or a reaction mixture pump into a circuit in which said aniline and said acid catalyst with or without previously added formaldehyde is circulated at a temperature of from 20 to 75° C., after feeding in at least 50% of the total amount of formaldehyde to be fed in, heating the reaction mixture for a period of at least 0.2 hours at a temperature above 75° C., the molar ratio of the aniline introduced to the total amount of formaldehyde to be added being from 1.7:1 to 7.2:1, neutralizing the resulting methylenedianiline, separating off water and aniline, phosgenating the purified methylenedianiline at a temperature of from 50 to 150° C. and a pressure of from 0.5 to 10 bar in the presence or absence of inert solvents, removing phosgene, HCl and optionally solvent from the crude MDI at a temperature below 150° C. possibly under vacuum or feeding in inert gas, then separating off said solvent from the isocyanate at a temperature of $\leq 190°$ C. and then separating off 2,2'-, 2,4'- and/or 4,4'-MDI and/or mixtures comprising at least two of these isomers by distillation at pressures of from 2 to 50 mbar and temperatures of from 150 to 250° C. and/or by crystallization.

11. A process for preparing monomeric MDI and polymeric MDI comprising crude MDI, wherein, in a semicontinuous process, aniline and acid catalyst are introduced, the ratio of said aniline to said acid catalyst being from 1:0.6 to 1:0.01, formaldehyde is fed through a nozzle or a reaction mixing pump into a circuit in which said aniline and said acid catalyst are circulated at a temperature of from 20 to 75° C., after the complete addition of the formaldehyde the reaction mixture is transferred to a storage vessel, heating for a period of from 0.1 to 120 min at a temperature of from 65 to 100° C., then the reaction mixture is heated in a reactor for a period of from 0.2 to 48 hours at a temperature from 105 to 150° C., the reaction mixture is neutralized at a temperature of from 60 to 110° C., the aqueous phase is separated off by phase separation, unreacted aniline is separated off from the organic phase by distillation, the purified monomeric MDA and polymeric MDA comprising crude MDA is phosgenated in the presence of an inert solvent at a temperature from 50 to 150° C. and a pressure of from 0.5 to 10 bar, phosgene, HCl and if appropriate solvent is removed from the process product, the crude MDI, at a temperature of from 50 to 149° C. and then solvent and, if present, chlorine compounds are separated off at a temperature of from 150 to 209° C.

12. A process for preparing polymeric MDI, wherein crude MDI is prepared according to claim 11 and monomeric MDI is separated off from the crude MDI by distillation at pressures of from 2 to 50 mbar and temperatures of from 150 to 250° C.

13. A process for preparing monomeric MDI, wherein crude MDI is prepared according to claim 11 and the monomeric MDI is separated off from the crude MDI by distillation at pressures of from 2 to 50 mbar and temperatures of from 150 to 250° C.

* * * * *